(12) United States Patent
Bohl et al.

(10) Patent No.: US 12,303,149 B2
(45) Date of Patent: *May 20, 2025

(54) APPARATUS FOR INCISION AND REMOVAL OF OSSEOUS TISSUE AND METHODS THEREOF

(71) Applicant: Dignity Health, San Francisco, CA (US)

(72) Inventors: Michael Bohl, Phoenix, AZ (US); Michael Mooney, Phoenix, AZ (US); Iridian Vaca, Madera, CA (US); Ryan Samuel Schulte, Spokane, WA (US); Andrew Robert Bruce, Bellingham, WA (US); Leah Elizabeth Fletcher, Shoreline, WA (US); Aron Lopez-Jimenez, Phoenix, AZ (US); Framarz Alam, Phoenix, AZ (US); Ethan Marshall, Queen Creek, AZ (US); Ivanna Revel, Scottsdale, AZ (US)

(73) Assignee: Dignity Health, San Francisco, CA (US)

( * ) Notice: Subject to any disclaimer, the term of this patent is extended or adjusted under 35 U.S.C. 154(b) by 24 days.

This patent is subject to a terminal disclaimer.

(21) Appl. No.: 18/498,957

(22) Filed: Oct. 31, 2023

(65) Prior Publication Data
US 2024/0058018 A1  Feb. 22, 2024

Related U.S. Application Data

(63) Continuation of application No. 17/386,928, filed on Jul. 28, 2021, now Pat. No. 11,839,387, which is a
(Continued)

(51) Int. Cl.
*A61B 17/17* (2006.01)
*A61B 17/15* (2006.01)
*A61B 17/16* (2006.01)

(52) U.S. Cl.
CPC .......... *A61B 17/1757* (2013.01); *A61B 17/15* (2013.01); *A61B 17/1671* (2013.01); *A61B 17/1604* (2013.01)

(58) Field of Classification Search
CPC .................. A61B 17/1757; A61B 17/1671
See application file for complete search history.

(56) References Cited

U.S. PATENT DOCUMENTS

| 6,358,254 B1 * | 3/2002 | Anderson | A61B 17/7071 |
| | | | 606/279 |
| 8,025,664 B2 * | 9/2011 | Farr | A61F 2/4611 |
| | | | 606/86 A |

(Continued)

OTHER PUBLICATIONS

Patent Cooperation Treaty, International Search Report and Written Opinion, International Application No. PCT/US2018/016256, Apr. 6, 2018, 8 pages.
(Continued)

*Primary Examiner* — Christian A Sevilla
(74) *Attorney, Agent, or Firm* — Polsinelli PC

(57) ABSTRACT

An apparatus for extraction of osseous tissue is disclosed. The apparatus includes a fixed portion and a clamp oriented along a generally central area of the fixed portion. The apparatus includes a first bone cutting device and a second bone cutting device coupled to the fixed portion and oriented around the clamp. The first bone cutting device and the second bone cutting device are coupled to the fixed portion using respective joints that accommodate orientations of the first bone cutting device and the second bone cutting device relative to the fixed portion along different horizontal and vertical axes. The clamp is configured to engage a first bone
(Continued)

portion during a surgical procedure. The first bone cutting device and the second bone cutting device are configured to remove a second bone portion.

11 Claims, 17 Drawing Sheets

Related U.S. Application Data continuation of application No. 16/481,535, filed as application No. PCT/US2018/016256 on Jan. 31, 2018, now Pat. No. 11,090,067.

(60) Provisional application No. 62/452,413, filed on Jan. 31, 2017.

(56) References Cited

U.S. PATENT DOCUMENTS

| | | | |
|---|---|---|---|
| 9,814,495 B2* | 11/2017 | Robie | A61B 17/1757 |
| 11,090,067 B2 | 8/2021 | Bohl et al. | |
| 2005/0267481 A1 | 12/2005 | Carl et al. | |
| 2005/0273167 A1 | 12/2005 | Triplett et al. | |
| 2006/0079908 A1* | 4/2006 | Lieberman | A61B 17/1757 606/99 |
| 2009/0312764 A1 | 12/2009 | Marino | |
| 2010/0023018 A1* | 1/2010 | Theofilos | A61B 17/1757 606/96 |
| 2010/0114100 A1 | 5/2010 | Mehdizade | |
| 2011/0301422 A1 | 12/2011 | Woolley et al. | |
| 2012/0022651 A1 | 1/2012 | Akyuz et al. | |
| 2015/0066088 A1 | 3/2015 | Brinkman et al. | |
| 2016/0270802 A1 | 9/2016 | Fang et al. | |
| 2017/0079666 A1* | 3/2017 | Wolinsky | A61B 17/15 |
| 2018/0271602 A1 | 9/2018 | Frey et al. | |
| 2021/0353310 A1 | 11/2021 | Bohl et al. | |

OTHER PUBLICATIONS

Canadian Intellectual Property Office, Office Action, Application No. 3,062,268, dated Apr. 19, 2024, 3 pages.

* cited by examiner

APPARATUS FOR INCISION AND REMOVAL OF OSSEOUS TISSUE AND METHODS THEREOF

CROSS REFERENCE TO RELATED APPLICATIONS

This is a continuation application of U.S. application Ser. No. 17/386,928, filed Jul. 28, 2021, which is a continuation application of U.S. 371 National patent application Ser. No. 16/481,535 filed Jul. 29, 2019, now U.S. Pat. No. 11,090,067, which claims benefit from International Application No. PCT/US2018/016256 filed Jan. 31, 2018, which claims benefit from U.S. Provisional Application No. 62/452,413 filed Jan. 31, 2017, all of which are herein incorporated by reference in their entireties.

FIELD

The present disclosure generally relates to medical apparatuses and devices, and in particular to surgical apparatuses configured for incision and extraction of osseous tissue that includes a clamp and bone cutting devices arranged along a fixed portion of the apparatus.

BACKGROUND

Various surgical procedures may involve the removal of osseous tissue, or bone. Such procedures may include, e.g., incisions along portions of the rib cage to gain access to the thoracic cavity, removal of bone tissue during knee surgery, or removal of portions of the skull or cutting of the skull during brain surgery. In most cases, precise and measurable cuts are required for each procedure. However, conventional devices typically employed for these procedures may lack precision and sufficient stabilization features, or have other drawbacks which may increase the likelihood of complications or concerns during surgery.

As one specific example, a laminectomy is a surgical procedure for removal of the vertebral arch, located in the cervical, thoracic, lumbar, and sacral regions of the spine. This procedure may be performed on patients with back pain due to compression along the spinal cord or nerves, which may be caused from various spine diseases, including (but not limited to) degenerative, infectious, neoplastic, traumatic, and congenital pathologies. Removal of the vertebral arch allows for decompression of the spinal canal, and gives the surgeon access to the contents of the spinal canal as needed. It is important when performing a laminectomy not to harm or tear the dura mater, which is a layer of tissue that surrounds and protects the spinal cord and nerve roots. A tear of the dura mater (fibrous sac containing the spinal cord, nerve roots, and spinal fluid) can result in cerebrospinal fluid leakage, which can potentially inhibit the body's healing process while also increasing the probability of an infection. With conventional surgical instruments used in this space, removal of the vertebral arch without causing a dural tear remains difficult. Further, such conventional instruments require an applied force to break through the vertebrae. This force is also generally unrestricted, thereby forfeiting the ability to control precision.

It is with these observations in mind, among others, that various aspects of the present disclosure were conceived and developed.

BRIEF DESCRIPTION OF THE DRAWINGS

Corresponding reference characters indicate corresponding elements among the view of the drawings. The headings used in the figures do not limit the scope of the claims.

DETAILED DESCRIPTION

Figure 1:
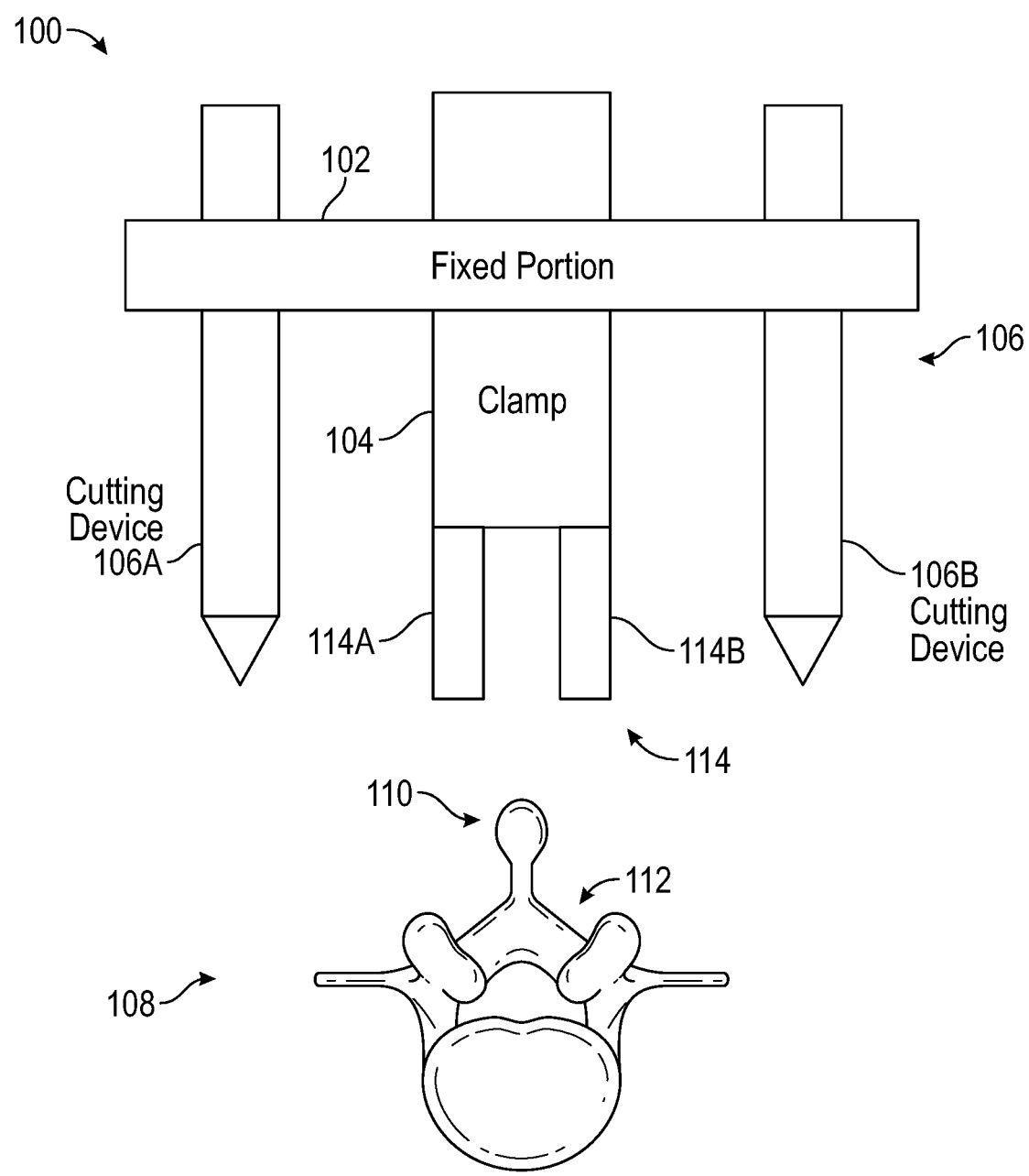
FIG. 1 is a simplified block diagram of an apparatus for incision and extraction of osseous tissue, according to aspects of the present disclosure.

Aspects of the present disclosure relate to an apparatus and related methods for incision and extraction of osseous tissue, which may also be referred to interchangeably herein as bone tissue. More specifically, an apparatus as described herein may include a fixed portion, a clamp mechanically coupled to the fixed portion for gripping bone tissue during a surgical procedure, and one or more (e.g., a plurality of) bone cutting devices arranged around the clamp along the fixed portion for cutting osseous tissue.

In some embodiments, the clamp, and the plurality of bone cutting devices may be engaged to the fixed portion using linear and spherical joints so that the clamp and bone cutting devices may be oriented along different horizontal and vertical axes relative to the fixed portion. Referring to the drawings, embodiments of an apparatus for incision and extraction of osseous tissue are illustrated and generally indicated as 100, 200, and 300 in FIGS. 1-18.

Referring to FIG. 1, a first embodiment of an apparatus, designated 100, includes a fixed portion 102, a clamp 104 coupled to the fixed portion 102, and a plurality of bone cutting devices 106, illustrated as cutting device 106A and cutting device 106B, that are coupled to the fixed portion 102 and oriented around the clamp 104, such that the clamp 104 is positioned between the cutting device 106A and the cutting device 106B. It should be understood that a pair of bone cutting devices 106 is shown solely for demonstration purposes, and some embodiments may include one bone cutting device or more than two bone cutting devices as needed for specific applications.

In some embodiments, the fixed portion 102 may comprise an elongated member, a rod, a linear guide rail, or a frame. The fixed portion 102 may be generally oriented to extend horizontally over a bone such as a vertebra 108 of a patient, including a spinous process 110 and lamina 112, as shown. During use, the fixed portion 102 generally rests in a fixed, stationary position relative to the other components of the apparatus 100 and the target bone, as described herein.

As shown, the clamp 104 may be coupled in a generally central position along the fixed portion 102. The clamp 104 may include any form of clamping device or vise-like apparatus capable of engaging and gripping a target area of bone tissue, such as the spinous process 110. In some embodiments, the clamp 104 may be coupled to the fixed portion 102 using a spherical joint or hinge joint (not shown) so that clamp 104 may be oriented along different horizontal and vertical axes relative to the fixed portion 102 or be configured with multiple degrees of freedom. In some embodiments, the clamp 104 may also be in linear sliding engagement along the fixed portion 102 (not shown). In other embodiments, the clamp 104 may be coupled to the fixed portion 102 using a vertically aligned support member (not shown). Yet in other embodiments, the clamp 104 may be fixed in a stationary position relative to the fixed portion 102.

In some embodiments, the clamp 104 includes at least a pair of clamp legs 114 illustrated as a first claim leg 114A and a second clamp leg 114B. The first clamp leg 114A and the second clamp leg 114B may be driven or moved together to bind or grip the spinous process 110 or other bone matter. Movement of the clamp legs 114 may be achieved by tightening a screw (not shown) in mechanical engagement with the clamp legs 114, or the clamp legs 114 may be spring loaded such that the clamp legs 114 are biased to a closed configuration, and may be driven to an open configuration by releasing the spring (not shown). Other suitable methods of moving the clamp legs 114 are contemplated and described herein. In other embodiments, a C-clamp may be implemented which is devoid of multiple legs and generally involves drawing a movable closing member against a stationary member to hold an object in place. Other such clamps are contemplated by the present inventive disclosure.

The bone cutting devices 106 are configured and operable to cut bone tissue and may include at least one of a drill, an osteotome, a rongeur, a scalpel, a laser, an ultrasonic device, a chisel, a saw, or the like, capable of creating an incision through osseous tissue to accomplish this function. In some embodiments, the bone cutting devices 106 may be coupled to the fixed portion 102 using spherical joints or hinge joints (not shown), so that the bone cutting devices 106 may be oriented and maintained along different axes or be mechanically configured with multiple degrees of freedom. In some embodiments, the bone cutting devices 106 may also be in linear sliding engagement along the fixed portion 102 (not shown). In some embodiments, the bone cutting devices 106 are configured so that cutting depths can be controlled; i.e., the surgeon may carefully control the depth of any incision into the bone tissue. Dimensions of the bone cutting devices 106 may also vary with respect to length and width as needed.

The apparatus 100 may enable surgeons to remove bone tissue safely and more efficiently. As one example, a neurosurgeon may employ the apparatus 100 to quickly and safely perform a laminectomy. Specifically, once a target vertebra has been exposed and is available for access, the clamp 104 of the apparatus 100 may be engaged to the spinous process 110 by driving the clamp legs 114 together and gripping the spinous process 110.

The surgeon may also align the bone cutting devices 106 along portions of the vertebra, and accurately position the bone cutting devices 106 over the lamina 112 in the position and angle desired. The bone cutting devices 106 may then be employed to form bilateral, controlled longitudinal incisions or cuts in order to remove the lamina 112 and/or the spinous process 110 from the vertebra 108. In the case where the bone cutting devices 106 include osteotomes, any force on the lamina 112 generated by application of the osteotomes is transmitted to the clamp 104, thereby canceling the force generated on the lamina 112 from the operation of the osteotomes so that the apparatus 100 remains in a stationary position relative to the vertebra 108 during the procedure.

Once incisions formed by the bone cutting devices 106 are advanced to a predefined appropriate depth, the lamina 112 may naturally release from the vertebra 108 and can be removed as a single piece with the spinous process 110 still attached to the clamp 104. Using the apparatus 100 as described, the dura mater surrounding the vertebra 108 underneath the lamina 112 is unlikely to be cut and the laminectomy procedure is efficient and precise in its application. In this example, the laminectomy procedure may be completed within a time span of one to three minutes or less. The apparatus 100 may involve primarily inexpensive mechanical components as opposed to software or electromechanical components. Aspects of the apparatus 100 may be formed using surgical steel, although the present disclosure is not limited in this regard.

Figure 2:
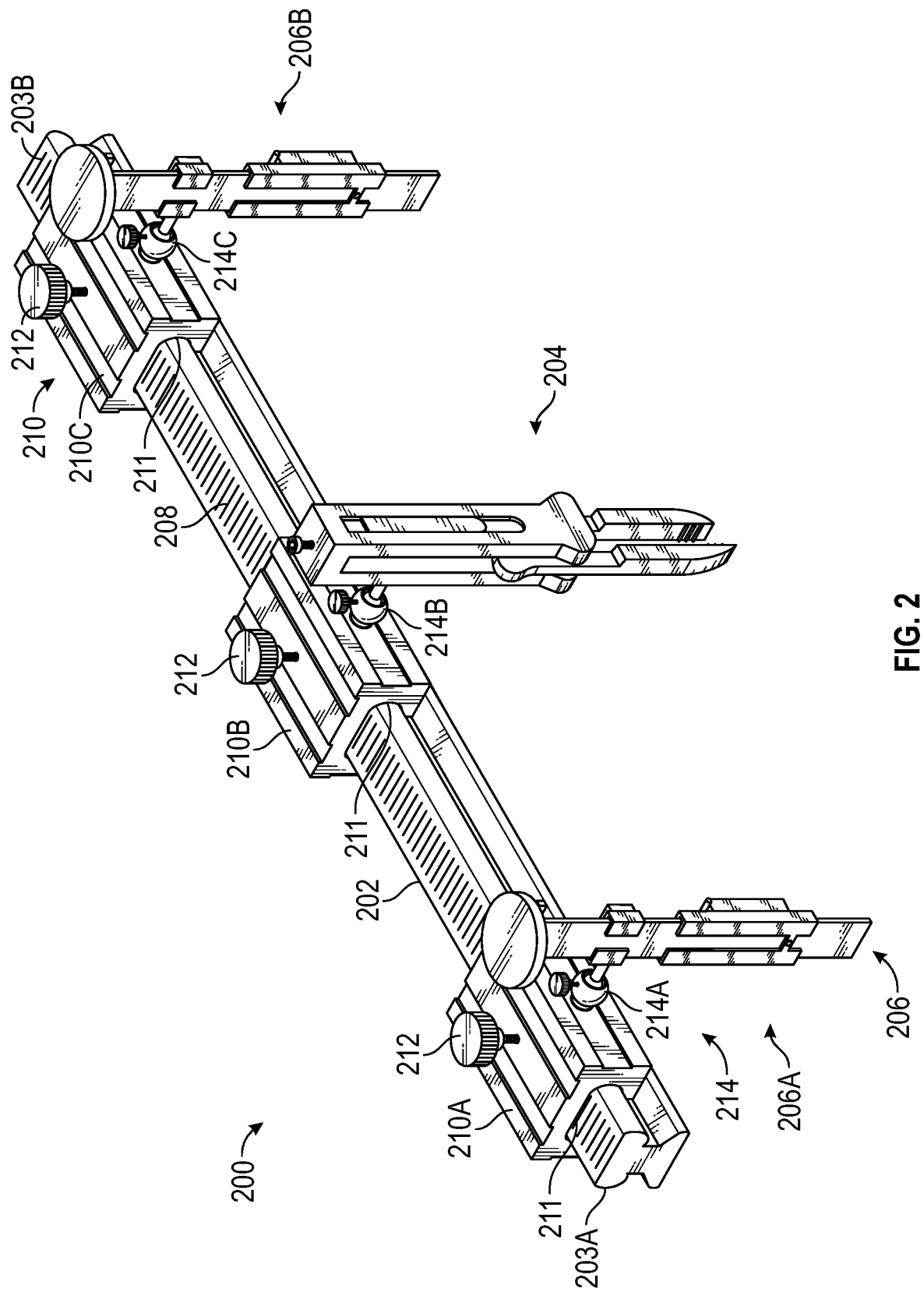
FIG. 2 is a perspective view of a first embodiment of an apparatus for incision and extraction of osseous tissue related to FIG. 1, according to aspects of the present disclosure.
Figure 3:
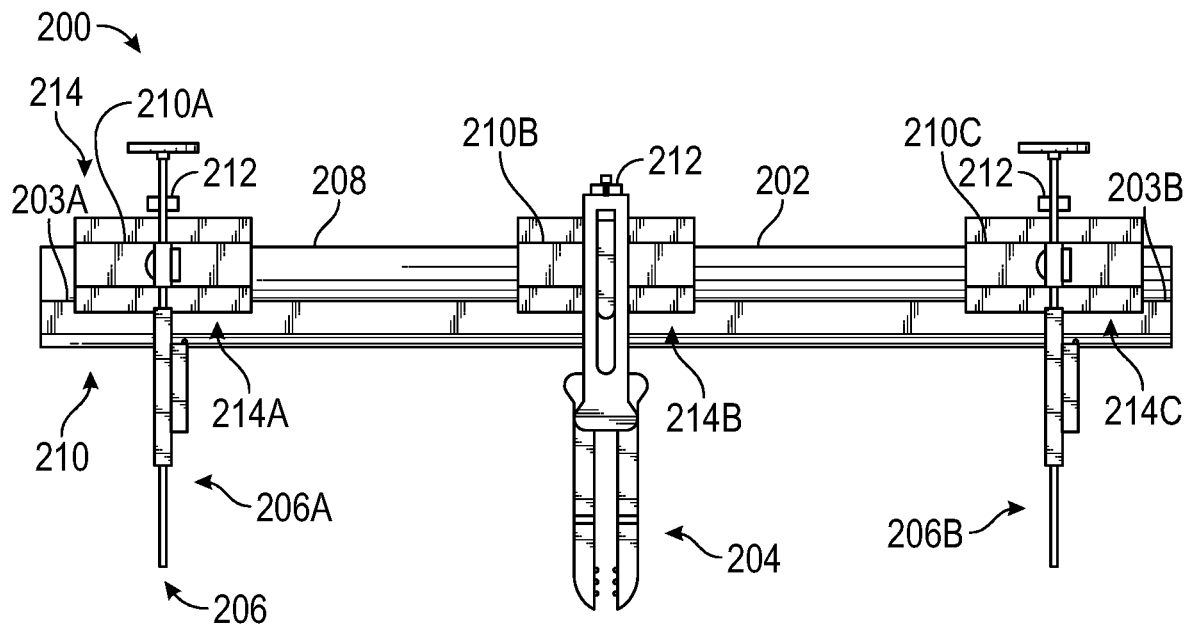
FIG. 3 is a front view of the apparatus of FIG. 2, according to aspects of the present disclosure.
Figure 4:
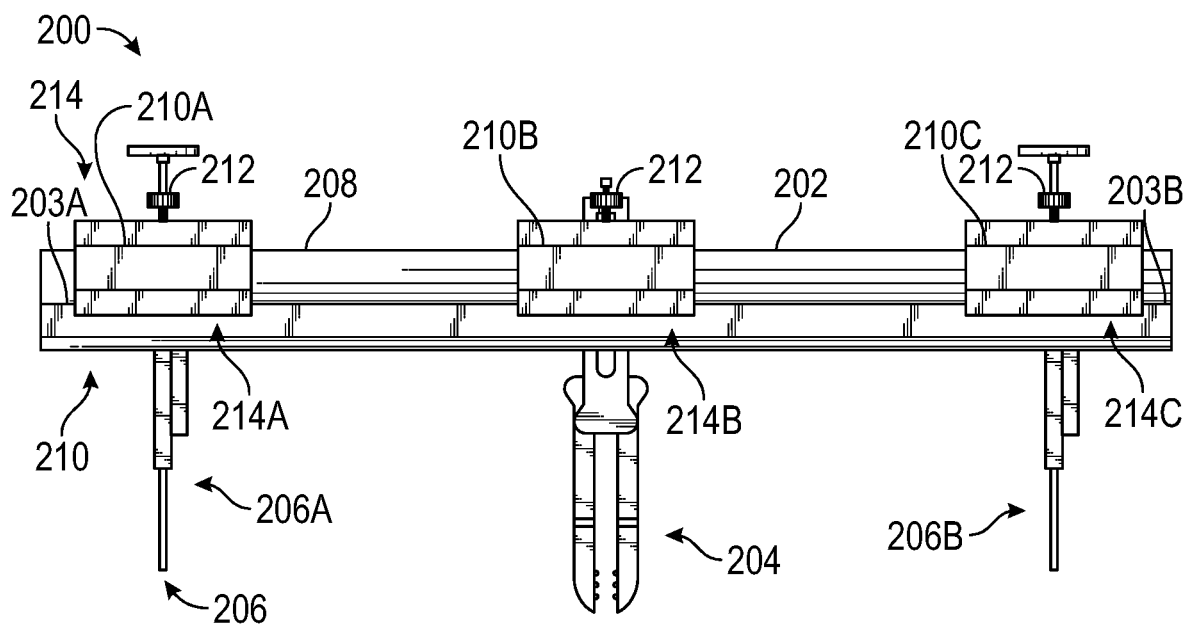
FIG. 4 is a rear view of apparatus of FIG. 2, according to aspects of the present disclosure.

Referring to FIGS. 2-4, one embodiment of an apparatus, designated 200, includes a fixed portion 202, a clamp 204 coupled to a generally central position along the fixed portion 202, and a plurality of osteotomes 206, illustrated as osteotome 206A and osteotome 206B, that are coupled to the fixed portion 202 and oriented generally adjacent to the clamp 204, such that the clamp 204 is positioned between the osteotome 206A and the osteotome 206B. It should be understood that a pair of osteotomes 206 and a sole clamp 204 are shown solely for illustrating possible aspects of the present disclosure, and some embodiments may include a plurality of clamps, a sole osteotome, or more than two osteotomes as may be suitable for specific applications. The osteotomes 206 and clamp 204 are described in greater detail below, but the osteotomes 206 illustrate one possible implementation of bone cutting devices previously described in FIG. 1 that may be configured to form incisions within bone in order to accommodate removal of bone tissue, and the clamp 204 may be generally configured to grip other bone tissue during surgery.

In some embodiments, the fixed portion 202 comprises a substantially linear rail, and may be generally cuboidal in shape, i.e. define an elongated three-dimensional rectangle shape as shown (although cylindrical/rod shapes and other such shapes are contemplated in related embodiments). The fixed portion 202 may be generally configured to extend horizontally over a bone such as the vertebra 108 of a patient during a laminectomy, similar to the orientation of the fixed portion 102 of the apparatus 100 relative to the vertebra 108 shown in FIG. 1. The fixed portion 202 defines a first end 203A, and a second end 203B opposite the first end 203A. In some embodiments, the fixed portion 202 defines a plurality of markers 208 arranged along the length of the fixed portion 202. The plurality of markers 208 may define etchings, labels, indentations, or the like and may be associated with units of measurement to assist a surgeon with arranging the clamp 204 and the osteotomes 206 over predetermined positions along the fixed portion 202, as further described herein.

In some embodiments, a plurality of carriages 210 may be mechanically coupled to the fixed portion 202 of the apparatus 200. In the present embodiment shown, the plurality of carriages 210 may be illustrated as carriage 210A, carriage 210B, and carriage 210C. In some embodiments, the carriage 210A is positioned generally along the first end 203A, the carriage 210C is positioned generally along the second end 203B, and the carriage 210B is positioned between the carriage 210A and the carriage 210C. Each of the carriages 210 may be oriented in linear sliding engagement along the fixed portion 202. Specifically, each of the carriages 210 may define a respective channel 211 extending through each of the carriages 210, and the carriages 210 may be slidably mounted along the fixed portion 202 by inserting either the first end 203A or the second end 203B of the fixed portion 202 through the channels 211 of the carriages 210. The plurality of carriages 210 may define linear bearings, slide casings, or linear/prismatic joints that are capable of linear sliding movement along the fixed portion 202, as further described herein. In some embodiments, as shown, the fixed portion 202 may be formed with linear guides or rails, and the channels 211 may be formed of a shape that is suitable for receiving the linear guides in order to movably mount and maintain the carriages 210 along the guide rails of the fixed portion 202, although the present disclosure is not limited in this regard.

In some embodiments, each of the carriages 210 may include a respective tightening knob 212 or other such locking mechanism for restricting linear movement of the carriages 210 along the fixed portion 202. In other words, when the tightening knob 212 of the carriage 210A is engaged, the tightening knob 212 maintains the carriage 210A in a locked or stationary position relative to the fixed portion 202. Maintaining the carriages 210 in a locked or stationary position relative to the fixed portion 202 may be advantageous during surgery when various forces may be exerted upon the apparatus 200, as further described herein.

As further shown, a plurality of spherical joints 214 may be mounted to or otherwise defined along the carriages 210. In particular, as illustrated, a spherical joint 214A may be included along the carriage 210A, a spherical joint 214B may be included along the carriage 210B, and a spherical joint 214C may be included along the carriage 210C. The spherical joints 214 may define ball joints, ball bearings, spherical bearings, ball and socket joints, or the like.

Figure 5:
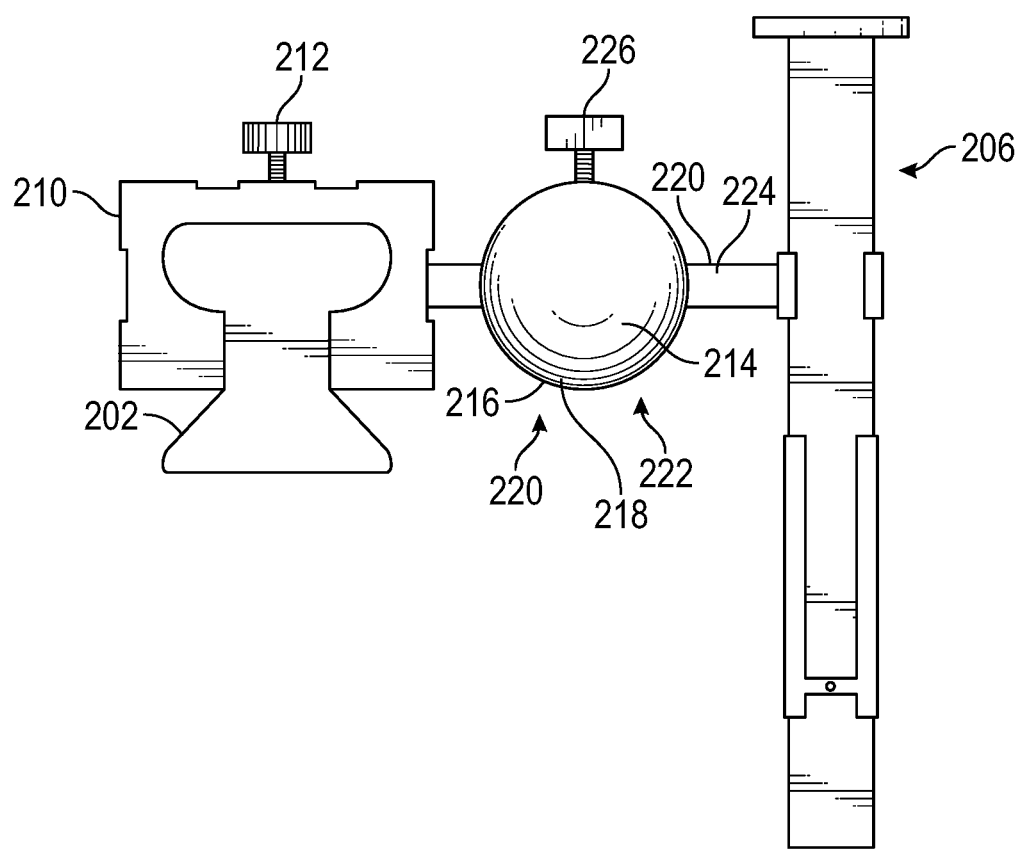
FIG. 5 is a side view of the apparatus of FIG. 2, according to aspects of the present disclosure.

Referring to FIG. 5, in some embodiments, each of the spherical joints 214 may include at least a housing body 216 defining a cavity 218, with the housing body 216 mounted or otherwise defined along the carriage 210 of the apparatus 200. The spherical joints 214 may further include a ball stud 220 defining a ball portion 222 in communication with a stem portion 224. The ball portion 222 of the ball stud 220 may be rotatably engaged within the cavity 218 of the housing body 216 to accommodate angular rotation of the stem portion 224 relative to the housing body 216 and enable multiple degrees of freedom. Further, as shown, the stem portion 224 may be coupled to or mounted along an osteotome 206 (or the clamp 204 (not shown)). In this manner, the osteotome 206 may be oriented along different horizontal and vertical axes, and may be rotated relative to the fixed portion 202 by nature of the osteotome 206 being coupled to the spherical joint 214.

In some embodiments as shown, the spherical joints 214 may include a tightening knob 226 or other like locking mechanism similar to the tightening knobs 212 for restricting movement of the ball stud 220 relative to the housing body 216. In other words, when the tightening knob 226 of a spherical joint 214 is engaged, the tightening knob 226 maintains the ball stud 220 in a substantially locked or stationary position relative to the housing body 216 and restricts angular and rotational movement thereof. Maintaining the ball stud 220 in a locked or stationary position relative to the housing body 216 may be advantageous during surgery when various forces may be exerted upon the apparatus 200 and it is desired to maintain the osteotomes 206 (and/or the clamp 204) in a stationary position.

Figure 6:
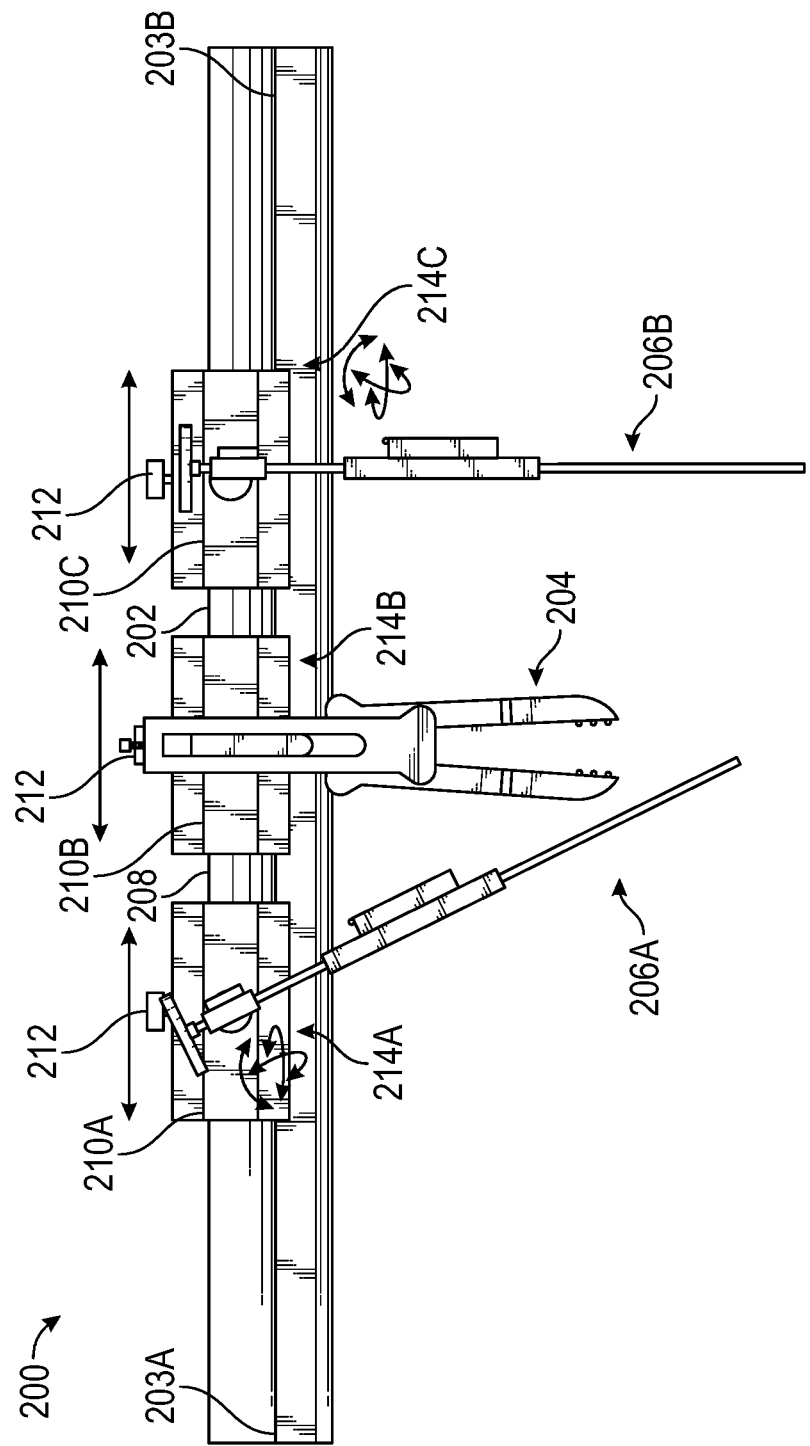
FIG. 6 illustrates possible movement of a plurality of bone cutting devices and a clamp of the apparatus of FIG. 2 relative to a fixed portion, according to aspects of the present disclosure.

Referring to FIG. 6, each of the clamp 204, the osteotome 206A, and the osteotome 206B, when coupled to any one of the spherical joints 214, may be configured with multiple degrees of freedom, i.e., may be oriented along different horizontal and vertical axes relative to the fixed portion 202. In addition, by virtue of the spherical joints 214 being coupled to the carriages 210, the linear positioning of each of the clamp 204, the osteotome 206A, and the osteotome 206B along the fixed portion 202 may be adjusted by sliding the carriages 210 to different predetermined positions along the fixed portion 202 as desired. For example, as indicated by the horizontal arrows of FIG. 6, the carriage 210A (and the osteotome 206A) may be advanced along the fixed portion 202 towards the first end 203A or the second end 203B to a predetermined position (not shown) as desired, and the tightening knob 212 defined along the carriage 210A may be actuated, tightened or otherwise engaged to lock the carriage 210A or otherwise maintain the carriage 210A in a substantially stationary configuration along the predetermined position. In addition, with the spherical joint 214A defined along the carriage 210 as described, and the osteotome 206A being coupled to the spherical joint 214A, the osteotome 206A may be oriented along different horizontal and vertical axes relative to the fixed portion 202 (as illustrated by the curved arrows), independently of the osteotome 206B and the clamp 204. The clamp 204, when coupled to the spherical joint 214B and the carriage 210B, and the osteotome 206B, when coupled to the spherical joint 214C and the carriage 210C, are capable of the same or similar movement. Once the components of the apparatus 200 (the clamp 204, the osteotome 206A, and the osteotome 206B) are oriented as desired, the surgeon may engage the tightening knobs 212 and the tightening knobs 226 (not shown in FIG. 6) to temporarily maintain these orientations during a surgical procedure. This enhanced flexibility, maneuverability, and stability of the apparatus 200 components may allow a surgeon to more accurately align the apparatus 200 along a vertebra or other bone tissue and safely complete a cutting procedure.

As one non-limiting example, referring to FIGS. 7A-7D, a neurosurgeon may employ the apparatus 200 to efficiently and safely perform a laminectomy. As shown, the apparatus 200 as described above includes the fixed portion 202 (defining the plurality of markers 208) with a plurality of carriages 210, designated 210A, 210B, and 210C, in movable engagement along the fixed portion 202 between the first end 203A and the second end 203B. In addition, the plurality of spherical joints 214, designated spherical joint 214A, spherical joint 214B, and spherical joint 214C are defined along the carriages 210A, 210B, and 210C respectively. The osteotome 206A is coupled to the spherical joint 214A and the carriage 210A, the osteotome 206B is coupled to the spherical joint 214C and the carriage 210C, and the clamp 204 is coupled to the spherical joint 214B and the carriage 210B. As further shown, the clamp 204 may define a pair of clamp legs 230, designated clamp leg 230A, and 230B. Cutting lines 232A-232B are exclusively shown in FIGS. 7B and 7C and further described below. In addition, FIGS. 7A-7D indicate that the osteotome 206A may define a blade 234A, and the osteotome 206B may define a blade 234B. The apparatus 200 may be oriented over the vertebra 108, which defines a spinous process 110 and lamina 112.

Figure 7A:
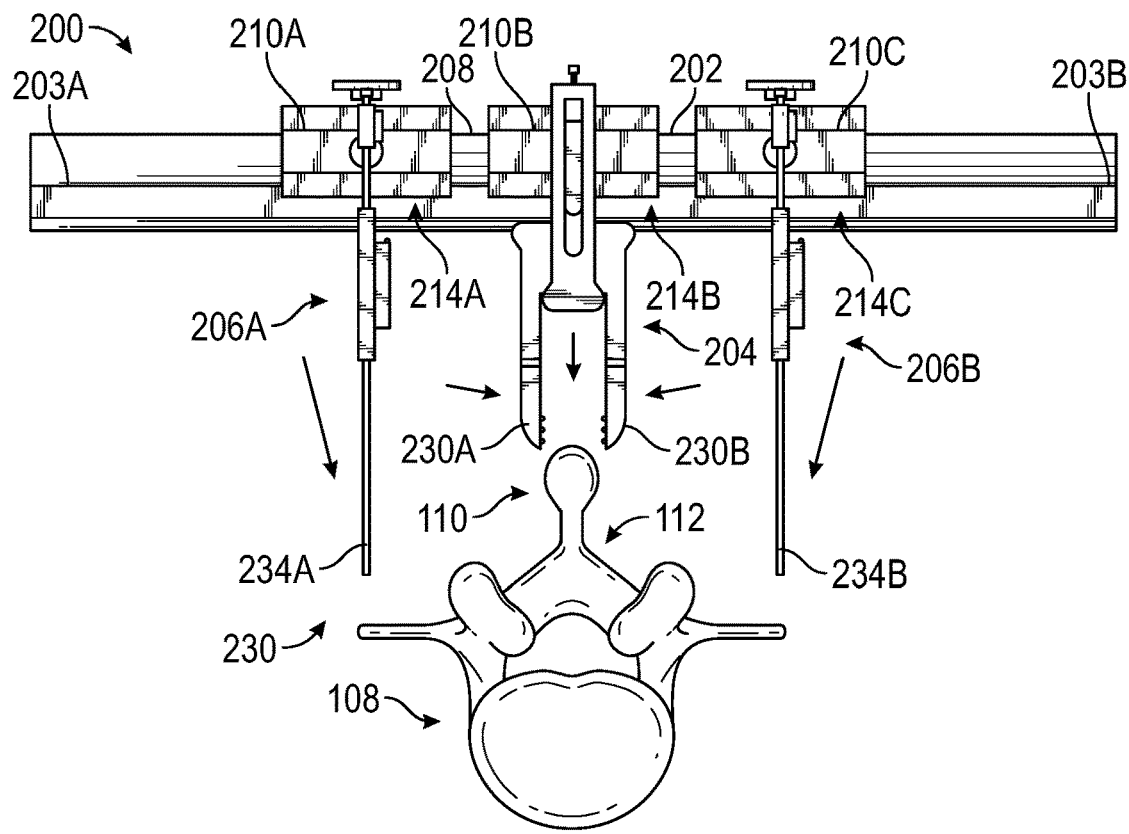
FIGS. 7A-7D illustrate different sequences of a laminectomy procedure which relate to one possible non-limiting use of the apparatus of FIG. 2, according to aspects of the present disclosure.

Referring specifically to FIG. 7A, once a target vertebra 108 has been exposed and is available for access, the apparatus 200 may be oriented over the spinous process 110 of the vertebra 108 as shown. The clamp 204 of the apparatus 200 may be engaged to the spinous process 110 by driving the clamp leg 230A and the clamp leg 230B together to grip the spinous process 110, and temporarily couple the apparatus 200 to the vertebra 108.

Figure 7B:
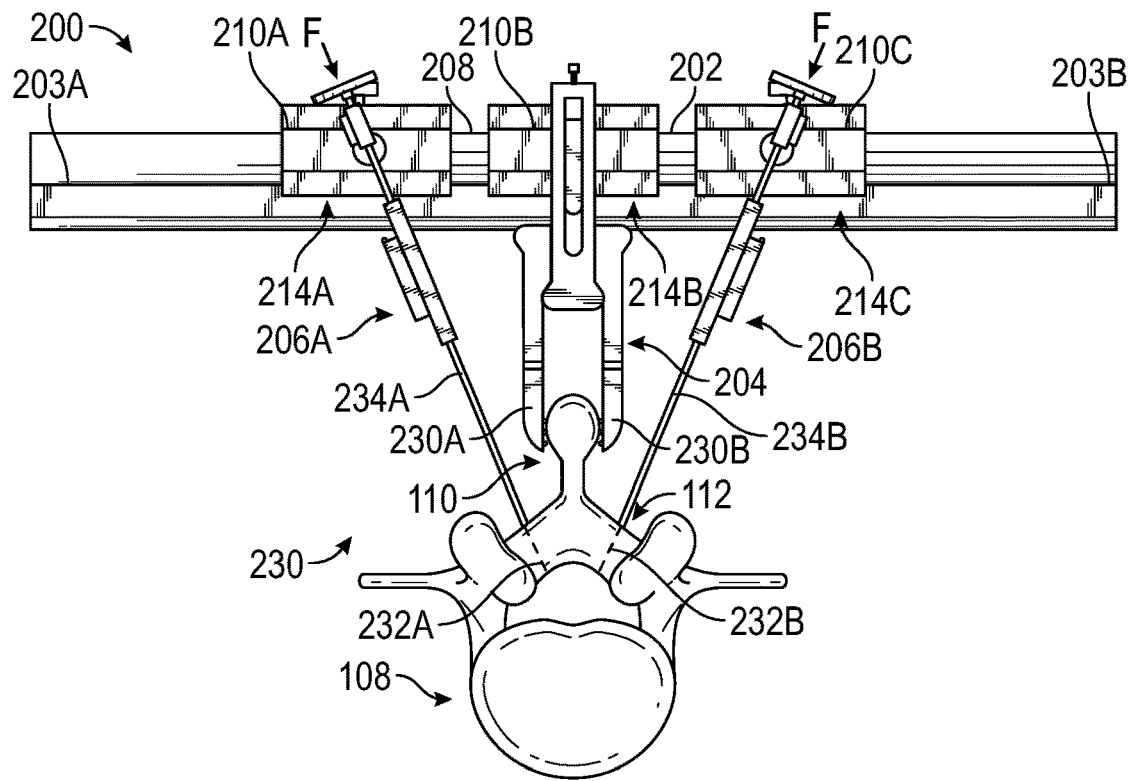
Figure 7C:
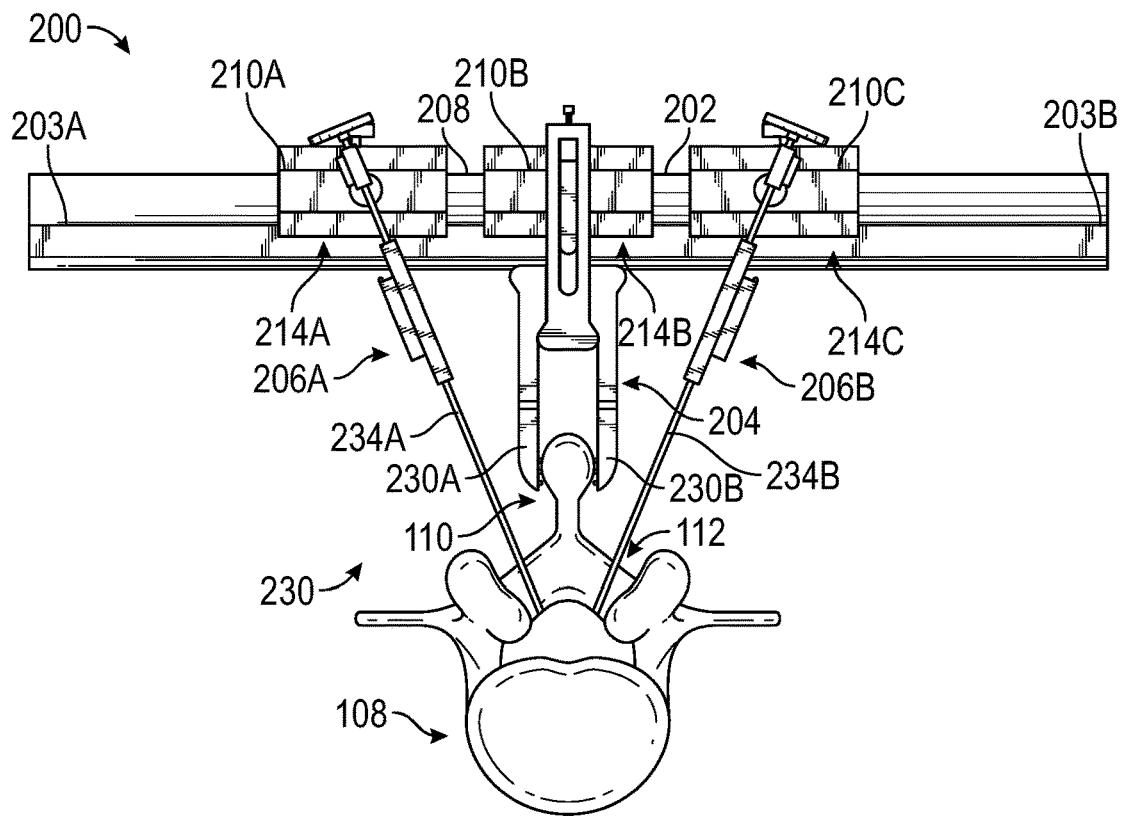

Referring to FIG. 7B, using the carriages 210, the surgeon may align the osteotomes 206 as desired between the first end 203A and the second end 203B of the fixed portion 202. Using the spherical joints 214, the osteotomes 206 may also be aligned along predetermined portions of the vertebra 108, or cutting lines designated 232A and 232B. Specifically, the blade 234A of the osteotome 206A may be aligned along the cutting line 232A, and the blade 234B of the osteotome 206B may be aligned along the cutting line 232B. Referring to FIGS. 7B-7C, a force, designated F may be applied to the upper portions of the osteotomes 206 to drive the blade 234A of the osteotome 206A in a downwards direction, and to also drive the blade 234B of the osteotome 206B in a downwards direction as indicated to form bilateral, controlled longitudinal incisions or cuts in order to remove at least a portion of the lamina 112 and/or the spinous process 110 from the vertebra 108, as defined by the cutting lines 232A and 232B. Forces exerted upon the lamina 112 during cutting by the osteotomes 206 is transmitted to the clamp 204, thereby canceling forces on the lamina 112 so that the apparatus 200 safely remains in a stationary position relative to the vertebra 108 during the procedure.

Figure 7D:
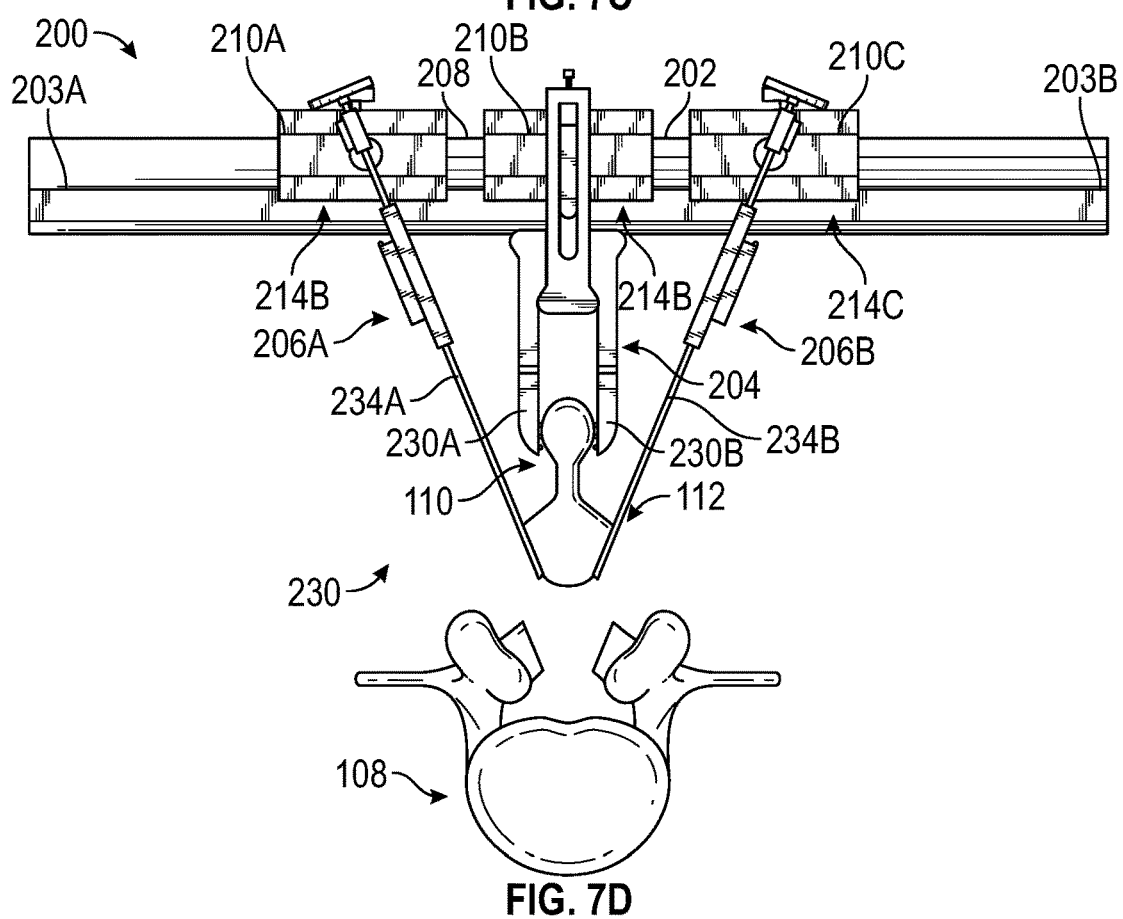
Figure 8:
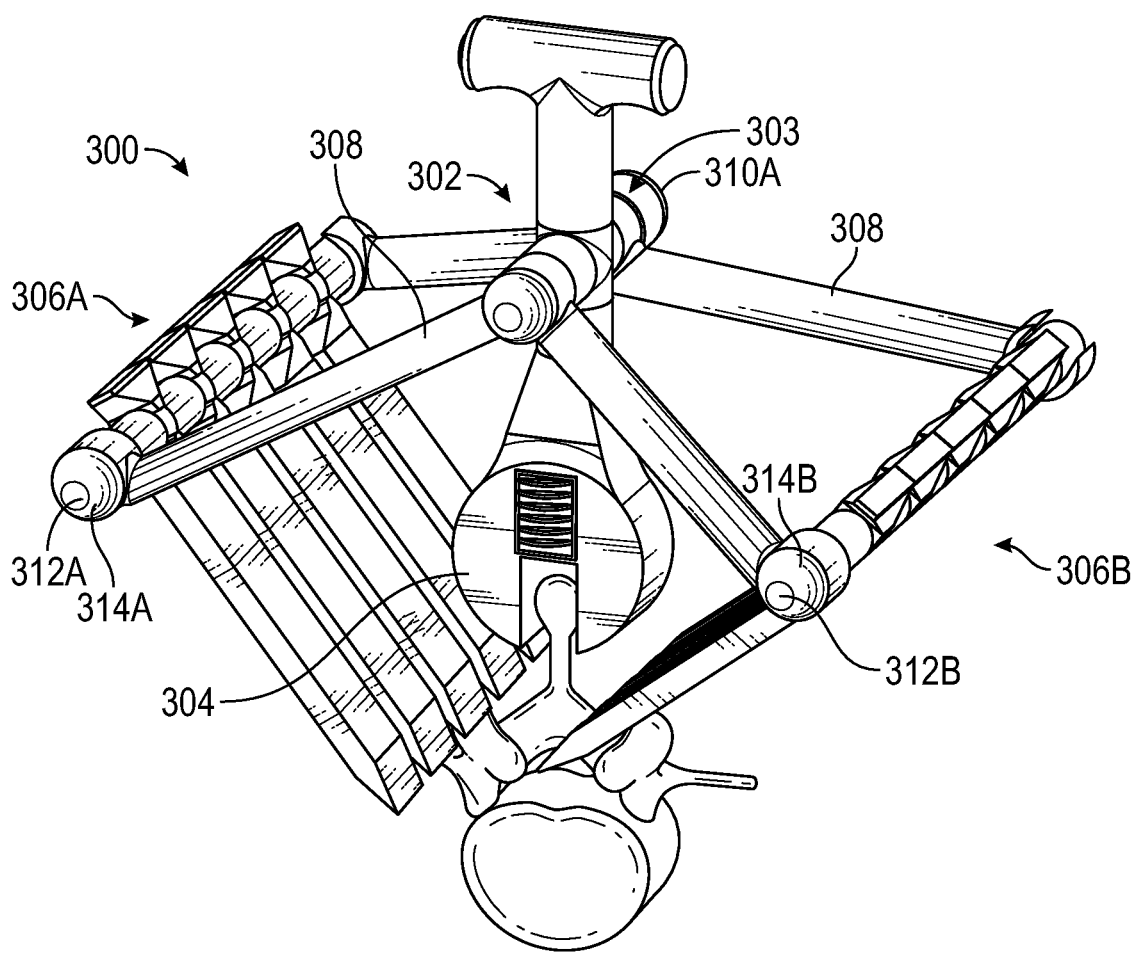
FIG. 8 is a perspective view of a second embodiment of an apparatus for incision and extraction of osseous tissue related to FIG. 1, according to aspects of the present disclosure.
Figure 9:
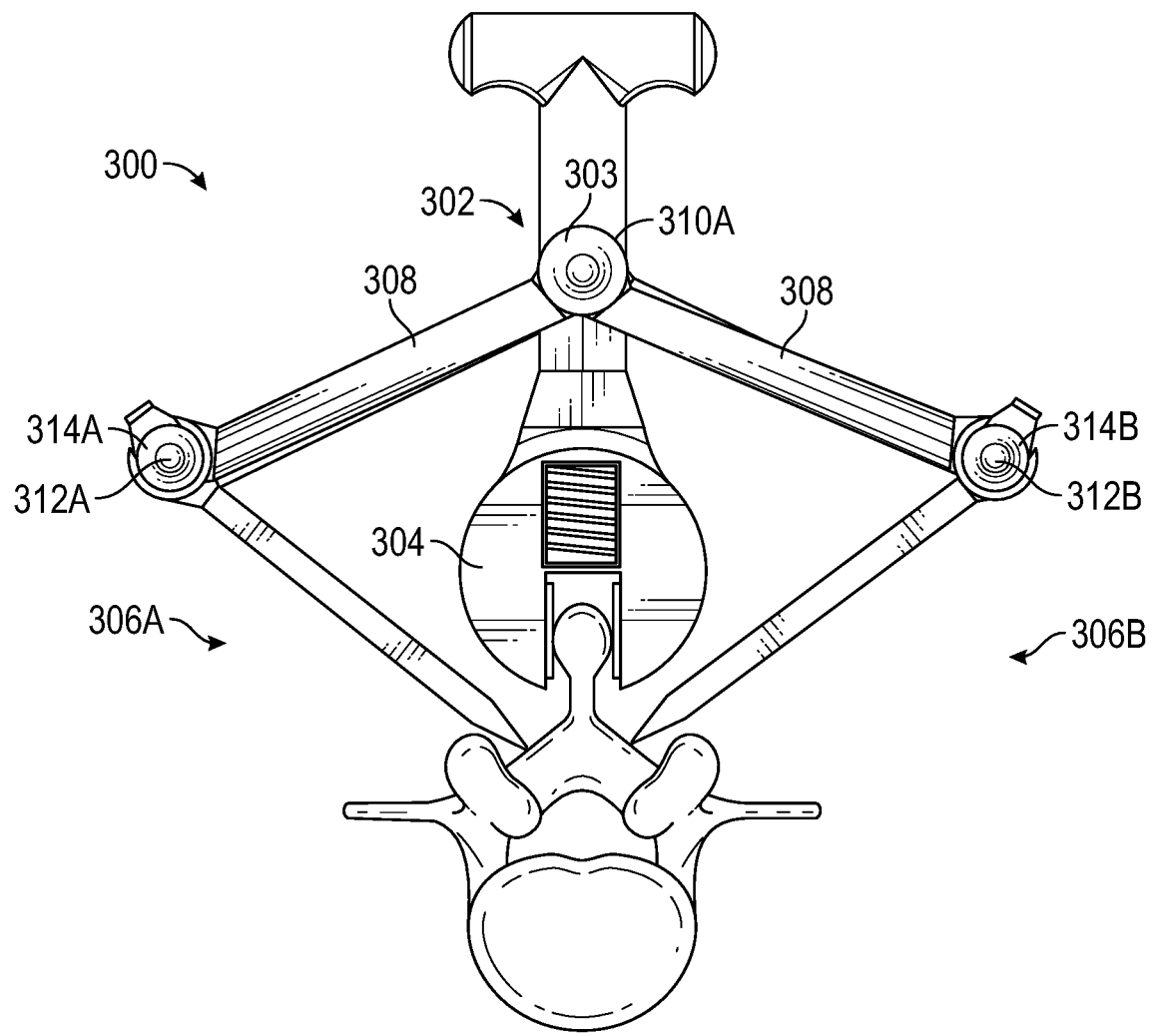
FIG. 9 is a front view of the apparatus of FIG. 8, according to aspects of the present disclosure.
Figure 10:
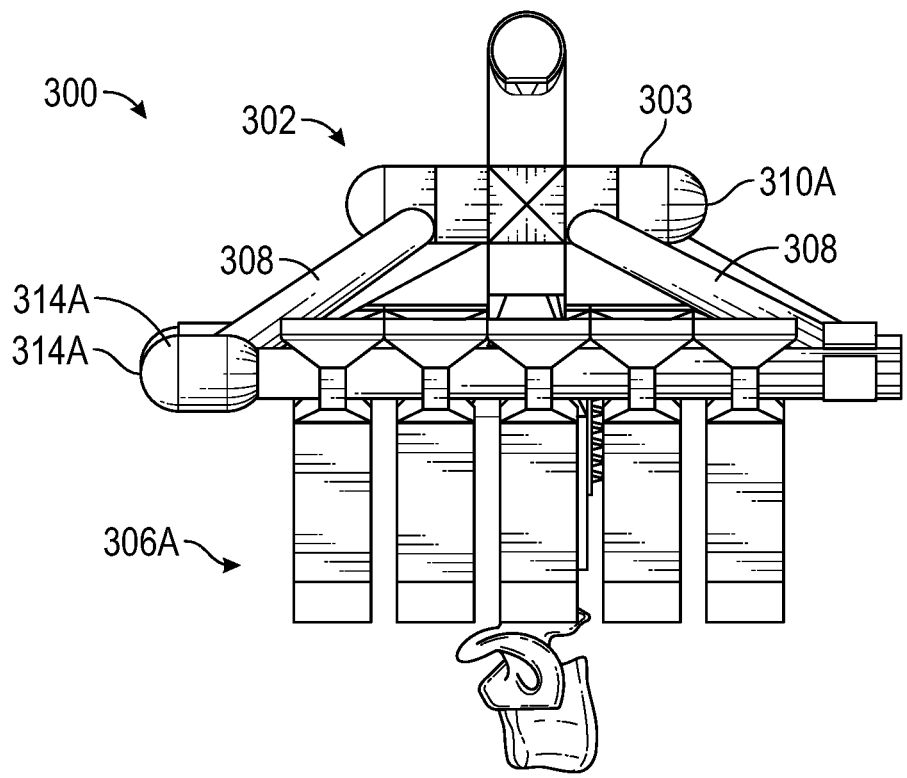
FIG. 10 is a side view of the apparatus of FIG. 8, according to aspects of the present disclosure.
Figure 11:
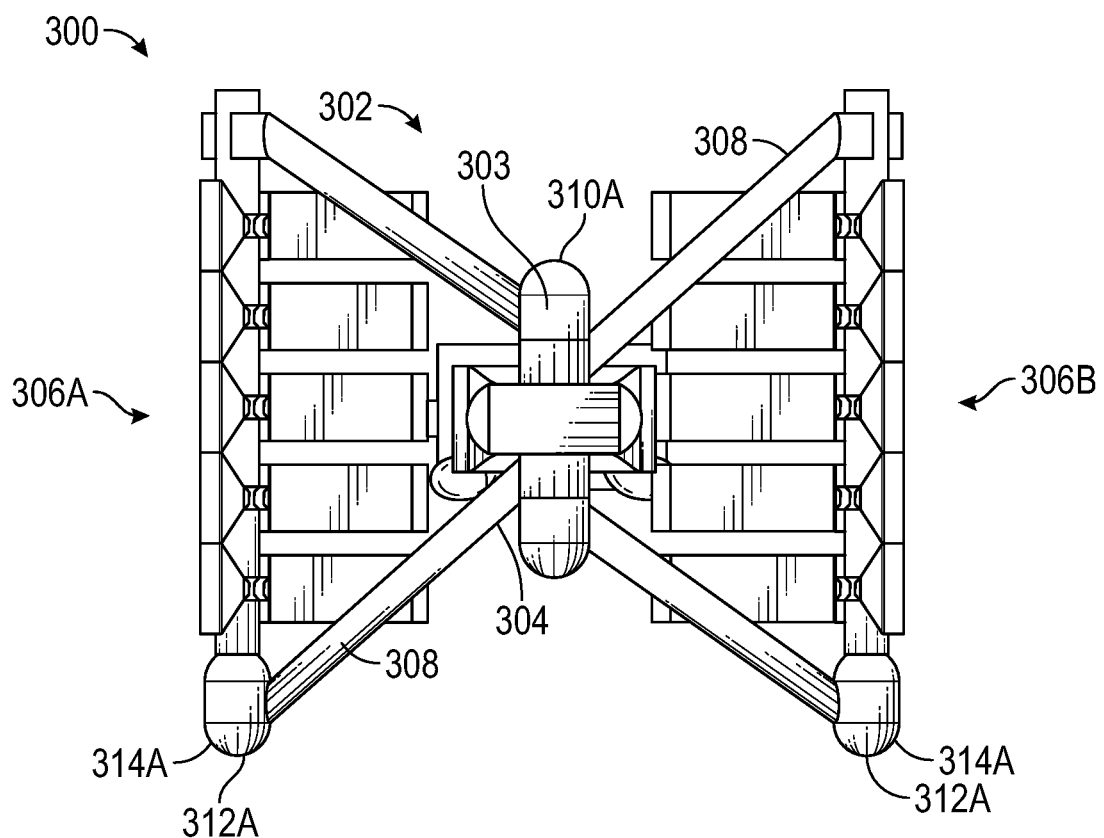
FIG. 11 is a top view of the apparatus of FIG. 8, according to aspects of the present disclosure.
Figure 12:
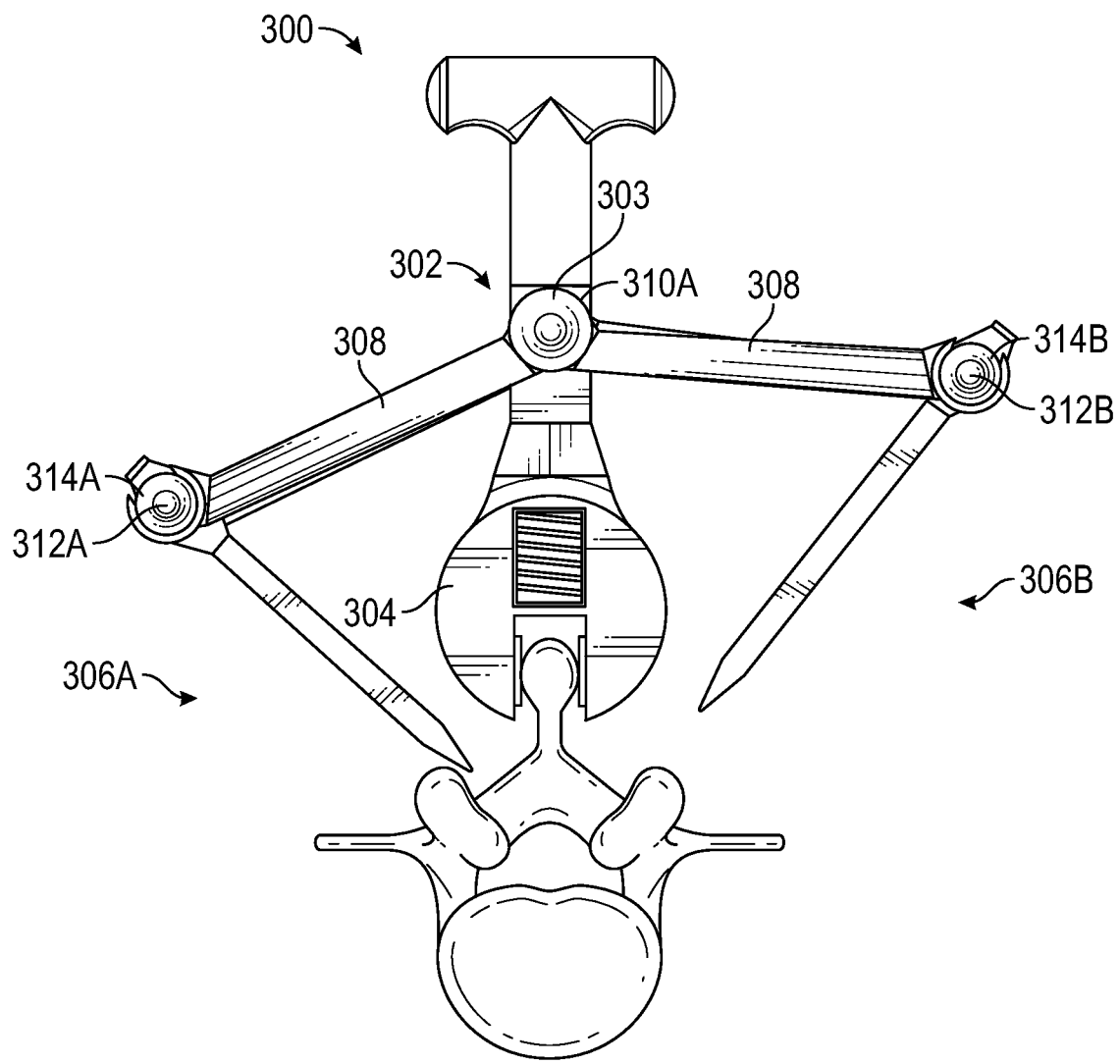
FIG. 12 illustrates possible movement of a plurality of bone cutting devices and a clamp of the apparatus of FIG. 8 relative to a fixed portion, according to aspects of the present disclosure.
Figure 13:
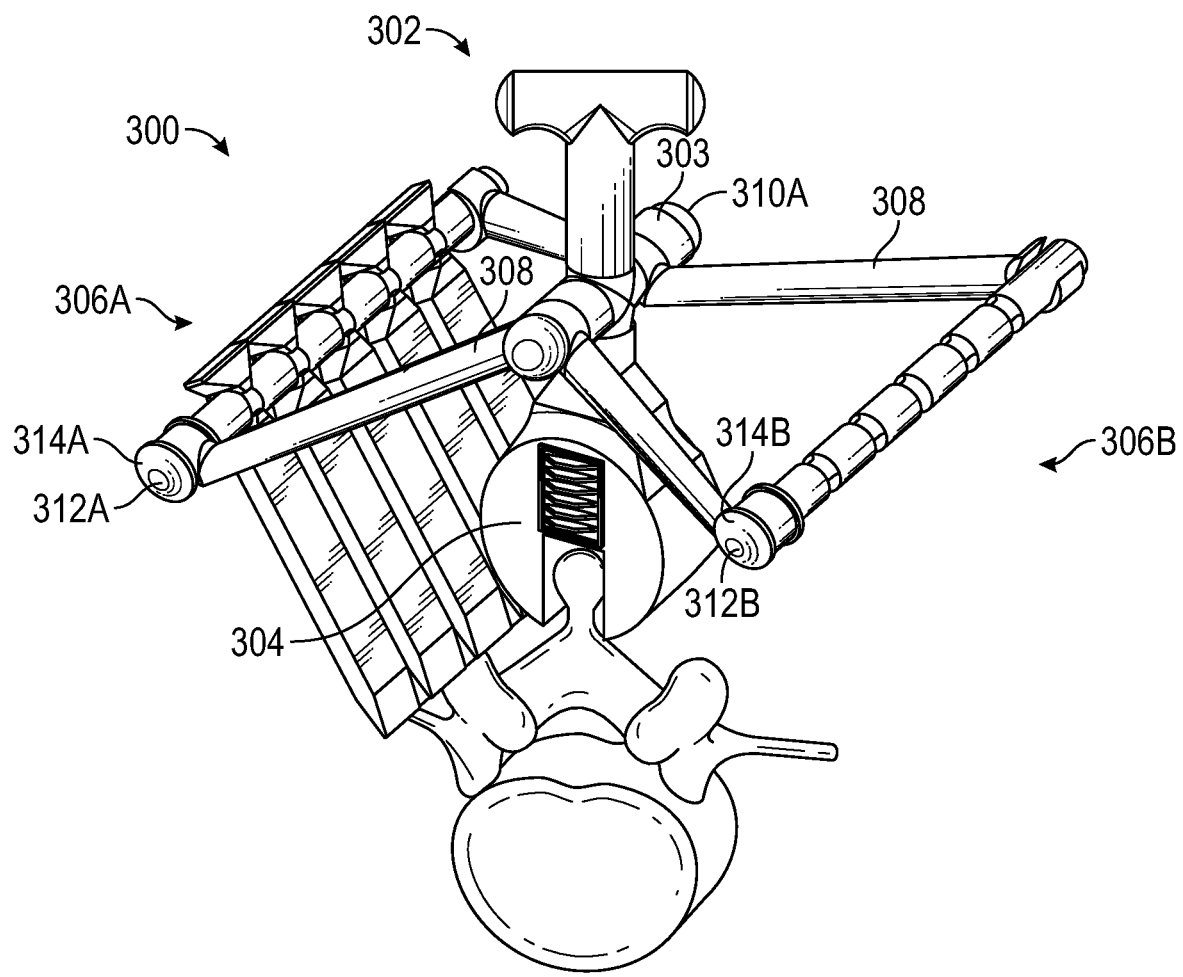
FIG. 13 is a perspective view of the apparatus of FIG. 8 with some of the bone cutting devices removed for illustrative purposes, according to aspects of the present disclosure.

Referring to FIGS. 7C-7D, once incisions formed by the osteotomes 206 are advanced to a predefined appropriate depth, at least a portion of the lamina 112 (defined by the cutting lines 232A and 232B shown in FIG. 7B) may naturally release from the vertebra 108 and can be removed as a single piece with the spinous process 110 still attached to the clamp 204 as shown. Using the apparatus 200 as described, the dura mater surrounding the vertebra 108 underneath the lamina 112 is unlikely to be cut and the laminectomy procedure is efficient and precise in its application. In this example, the laminectomy procedure may be completed within a time span of one to three minutes or less. The apparatus 200 may involve primarily inexpensive mechanical components as opposed to software or electromechanical components. Aspects of the apparatus 200 may be formed using surgical steel, or biocompatible polymers, although the present disclosure is not limited in this regard.

Referring to FIGS. 8-13, another embodiment of an apparatus, designated 300, for incision and extraction of osseous tissue generally includes a fixed portion 302, a clamp 304 in communication with the fixed portion 302, a plurality of bone cutting devices 306A defined along one side of the apparatus 300, and a plurality of bone cutting devices 306B defined along an opposite side of the apparatus 300 as shown, such that the clamp 304 is positioned between the plurality of bone cutting devices 306A and 306B. While a plurality of bone cutting devices 306A and 306B is illustrated, other embodiments may include a pair of bone cutting devices, i.e., a sole bone cutting device arranged along opposite sides of the apparatus 300.

As shown, the fixed portion 302 defines a generally central area of the apparatus 300, and is in direct communication with the clamp 304. In some embodiments, the fixed portion 302 includes a central rod 303 extending horizontally over the clamp 304. A plurality of arms 308 may be rotatably coupled to the central rod 303 of the fixed portion 302 by way of joints 310A. Joints 310A may be hinge joints, or revolute joints that provide single axis rotation of the arms 308 relative to the rod 303 of the fixed portion 302. In some embodiments, the fixed portion 302 may define a handle along the central rod 303 that may assist a surgeon to remove the apparatus 300 from a surgical area.

In addition, in some embodiments, the bone cutting devices 306A may be arranged along a lateral rod 312A, and the bone cutting devices 306B may be arranged along a lateral rod 312B. Specifically, the bone cutting devices 306A may be coupled to the lateral rod 312A by way of joints 314A, and the bone cutting devices 306B may be coupled to the lateral rod 312B by way of joints 314B. The joints 314, like the joints 310, may be hinge joints, or revolute joints that provide single axis rotation of the bone cutting devices 306 relative to the lateral rods 312A and 312B. As further shown, the arms 308 may connect the central rod 303 with the lateral rod 312A and the lateral rod 312B.

The bone cutting devices 306 of the apparatus 300 may include chisel tools as shown, which may be driven into bone tissue during e.g. a laminectomy or similar procedure; however the bone cutting devices 306 may also include osteotomes, scalpels, or other cutting tools. In some embodiments, the clamp 304 is spring-loaded such that arms (not shown) defined along the clamp 304 are biased to a closed position and may be temporarily engaged to an open position to grip bone tissue during procedures.

Figure 14:
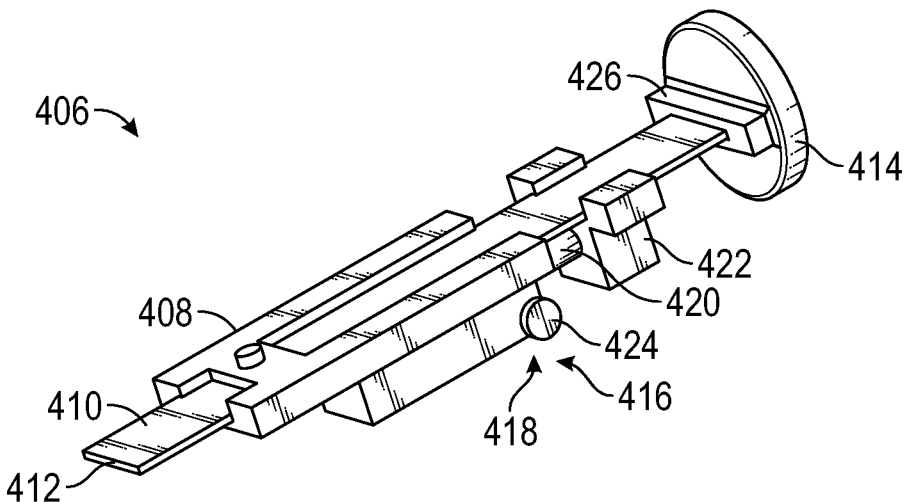
FIG. 14 is a perspective view of a first embodiment of a bone cutting device, specifically, an osteotome for use with the apparatus of FIG. 2 or FIG. 8, according to aspects of the present disclosure.
Figure 15:
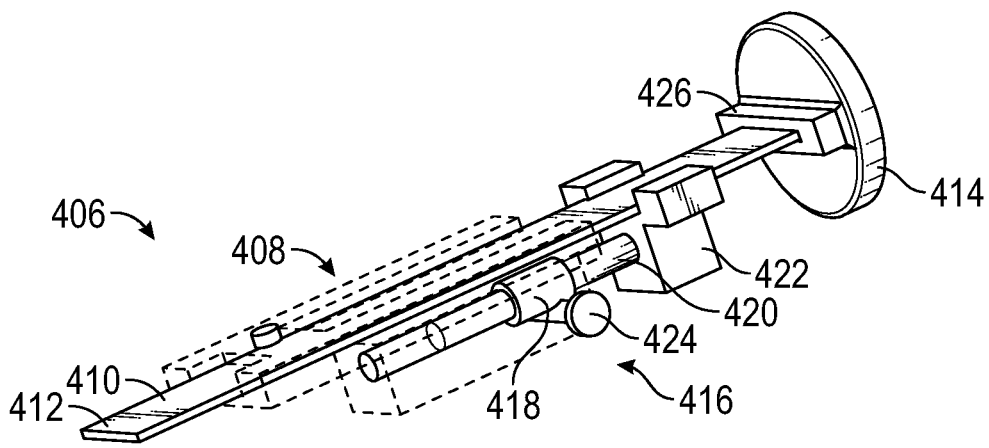
FIG. 15 is another perspective view of the osteotome of FIG. 14 with some portions revealed to illustrate a cutting adjustment mechanism, according to aspects of the present disclosure.

Referring to FIGS. 14-15, one embodiment of an osteotome 406, which may be identical to or similar to the osteotome 206, and may be used with the apparatus 200 or apparatus 300, is illustrated. The osteotome 406 is generally configured for driving a blade into bone tissue and making predetermined controlled cuts, and includes a mechanism for adjusting the depth of cuts formed by the blade using a stopper, as described herein. Specifically, the osteotome 406 includes a housing 408, and a blade 410 extending through opposite ends of the housing 408 such that the blade 410 is integrated into the housing 408. A cutting edge 412 may be defined along one end of the blade 410 and configured for making incisions into bone tissue, and a mallet end 414 may be defined along another end of the blade 410 opposite the cutting edge 412, and configured for receiving a blunt force of a mallet or other blunt object (not shown) for driving the blade 410 partially through the housing 408 and to within bone tissue.

In some embodiments, the osteotome 406 includes an adjustment mechanism 416 defined along the housing 408 for controlling the depth of cuts made using the blade 410. The adjustment mechanism 416 may include a self-locking worm gear 418 encapsulated within the housing 408 in which the gear 418 has been modified to have an internally threaded hole (not shown). The adjustment mechanism 416 may further include an externally threaded rod 420 passed through and configured to engage with the internally threaded hole of the self-locking worm gear 418. The externally threaded rod 420 may further be in communication with a stopper 422 as shown.

Figure 16:
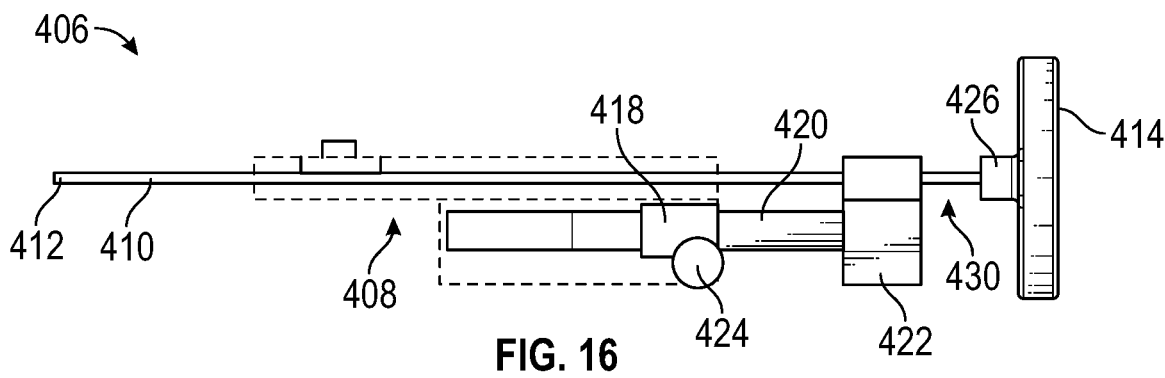
FIG. 16 is a side view of the osteotome of FIG. 14 illustrating adjustment of cutting depth, according to aspects of the present disclosure.

In addition, the adjustment mechanism 416 may include an adjustment knob 424. The adjustment knob 424 may be utilized to shift the externally threaded rod 420 back and forth through the self-locking worm gear 418 to predetermined positions in order to adjust the distance between the mallet end 414 and the stopper 422. Specifically, in some embodiments, rotation of the adjustment knob 424 may cause rotation of the self-locking worm gear 418 which may shift the externally threaded rod 420 (and the stopper 422) back and forth along the housing 408 relative to the self-locking worm gear 418. In some embodiments, a stopper surface 426 is defined along the mallet end 414 and configured to make contact with the stopper 422. Referring to FIG. 16, a cutting depth 430 associated with the osteotome 406, and defined by the distance between the stopper surface 426 and the stopper 422, may be modified by actuating the adjustment knob 424 to increase or decrease the distance between the stopper 422 and the stopper surface 426.

Figure 17A:
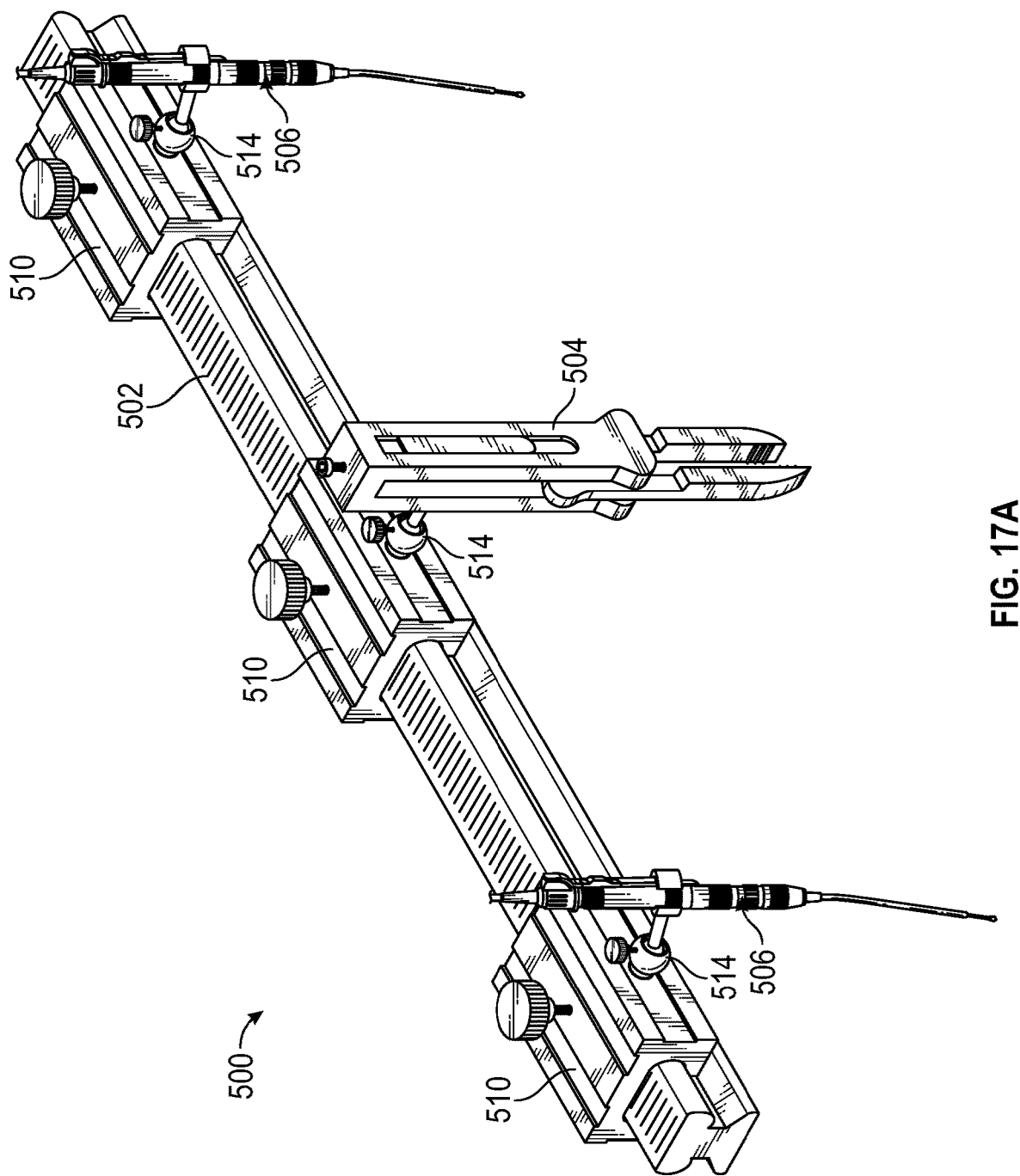
FIG. 17A is a perspective view of a third embodiment of an apparatus for incision and extraction of osseous tissue including a second embodiment of a bone cutting device, according to aspects of the present disclosure.
Figure 17B:
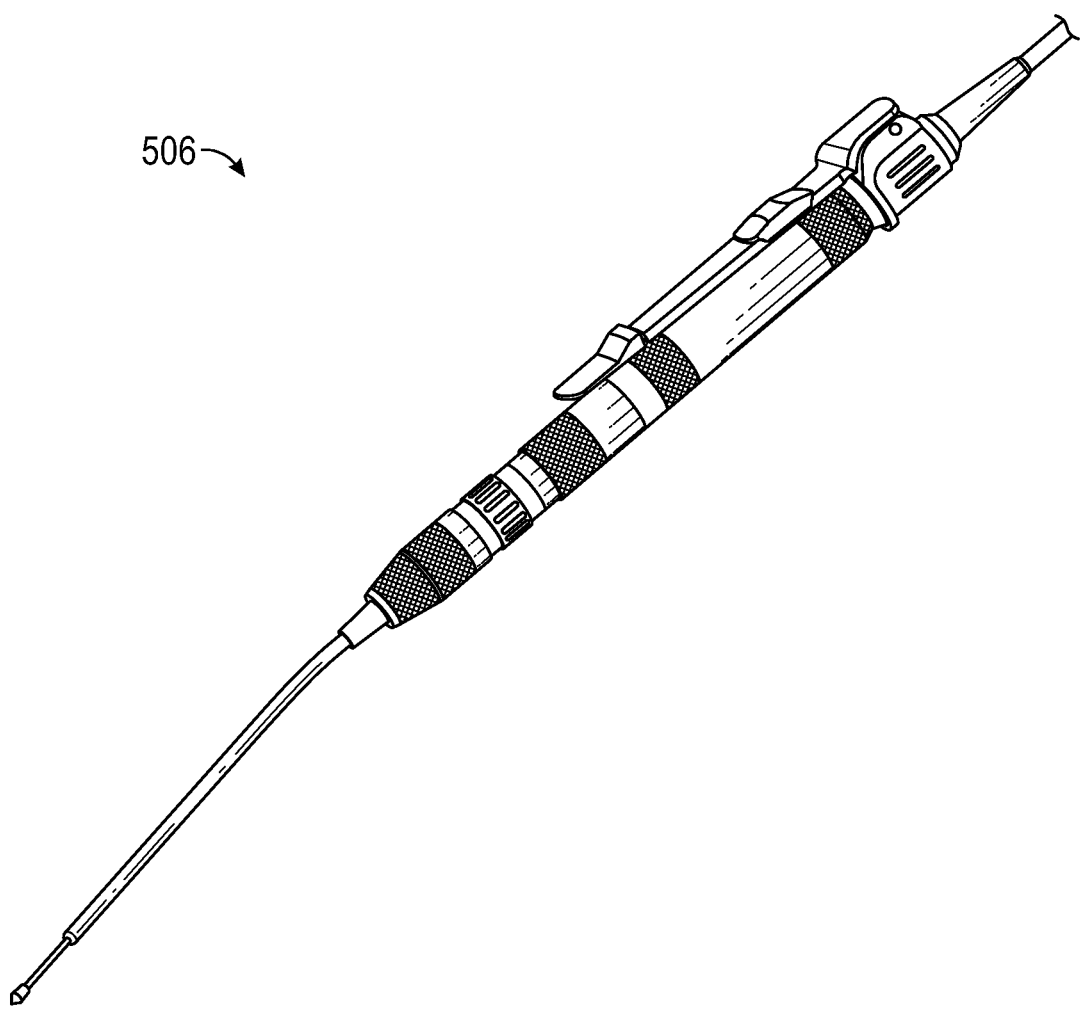
FIG. 17B is a perspective view of the second embodiment of a bone cutting device of FIG. 17A, according to aspects of the present disclosure.

Referring to FIGS. 17A and 17B, a third embodiment of an apparatus, designated 500, may generally include a fixed portion 502 similar to the fixed portion 202, and a clamp 504 similar to the clamp 204 arranged along a generally central position associated with the fixed portion 502. A plurality of surgical drills 506 may be arranged around the clamp 504 along the fixed portion 202. As shown, the clamp 504 and the surgical drills 506 may be coupled to the fixed portion 502 using spherical joints 514 and carriages 510 similar to the apparatus 200, so that the surgical drills 506 and the clamp 504 may be positioned along different vertical and horizontal axes relative to the fixed portion 502.

Figure 18A:
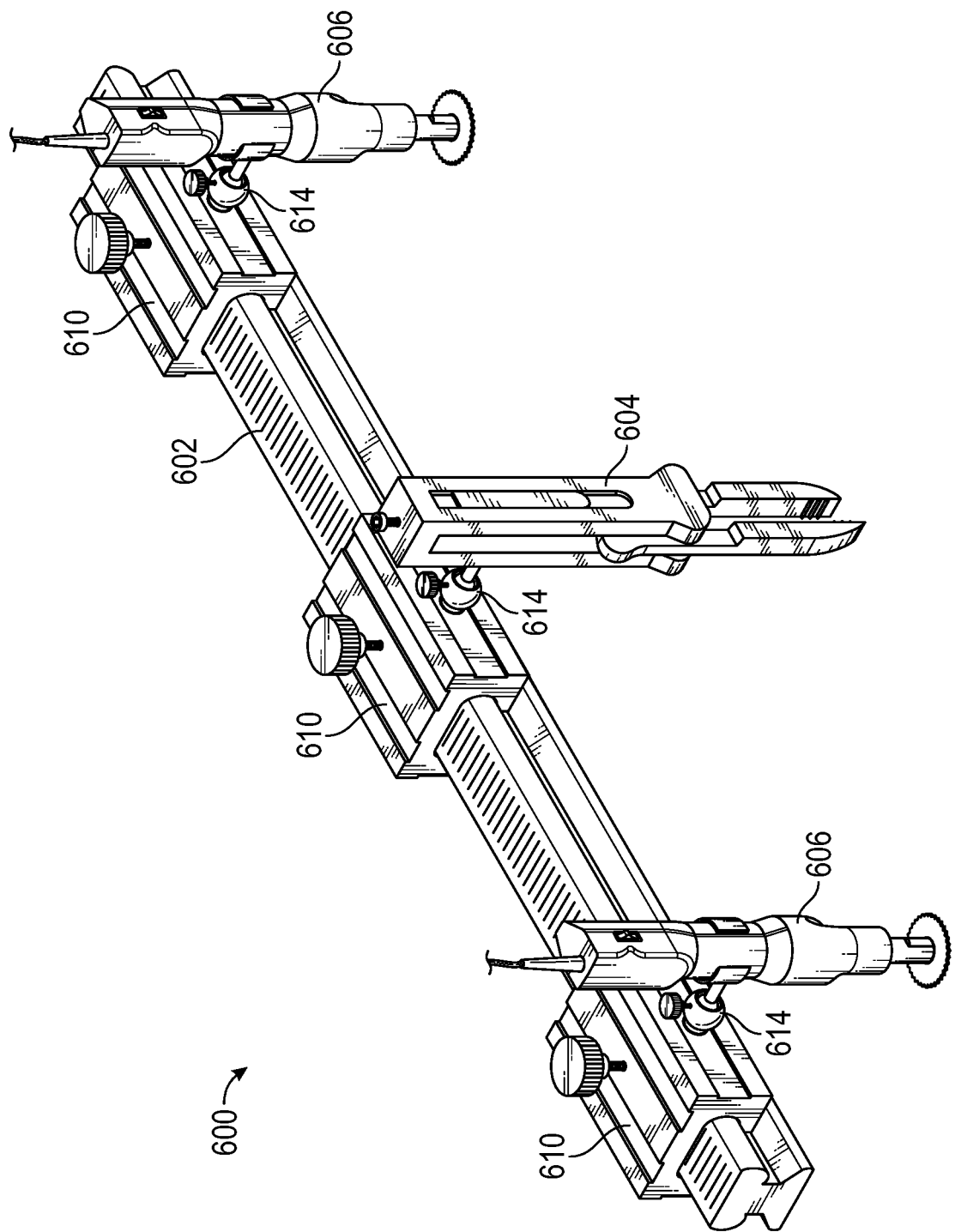
FIG. 18A is a perspective view of a fourth embodiment of an apparatus for incision and extraction of osseous tissue including a third embodiment of a bone cutting device, according to aspects of the present disclosure.
Figure 18B:
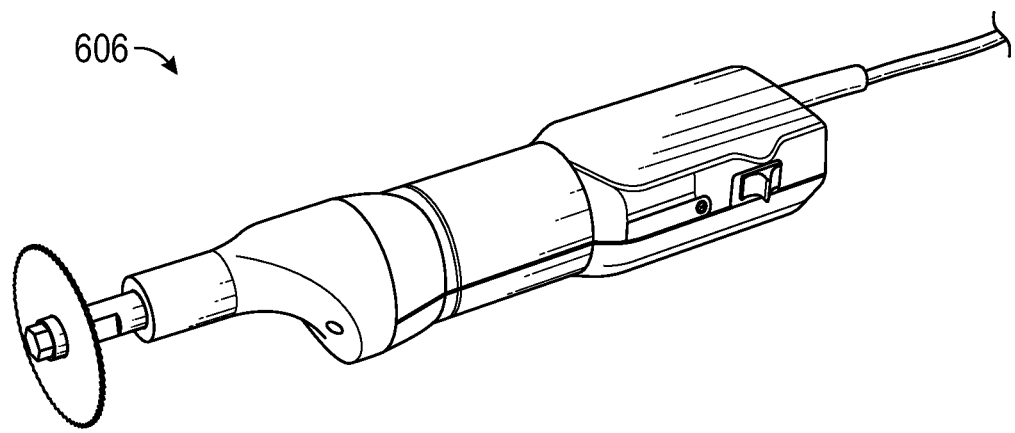
FIG. 18B is a perspective view of the third embodiment of a bone cutting device of FIG. 18A, according to aspects of the present disclosure.

Referring to FIGS. 18A and 18B, a fourth embodiment of an apparatus, designated 600, may generally include a fixed portion 602 similar to the fixed portion 202, and a clamp 604 similar to the clamp 204 arranged along a generally central position associated with the fixed portion 602. A plurality of surgical saws 606 may be arranged around the clamp 604 along the fixed portion 602. As shown, the clamp 604 and the surgical saws 606 may be coupled to the fixed portion 602 using spherical joints 614 and carriages 610 similar to the apparatus 200, so that the surgical saws 606 and the clamp 604 may be positioned along different vertical and horizontal axes relative to the fixed portion 602.

Other embodiments and features not shown are contemplated by the present disclosure. For example, in some embodiments, the clamp 204 of apparatus 200 may be replaced with a spring-clamp which applies inward pressure to the spinous process 110 using a spring. Alternatively, the fixed portion 202 may be coupled to bone tissue by drilling one or more holes into the spinous process, and passing rods through the holes. In other embodiments, a crank, motor, or other precise advancing tool may be implemented to gradually and in a controlled fashion drive osteotome blades or other cutting tools into bone tissue.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. An apparatus for surgical incision and extraction, comprising:
   an elongated member;
   one or more carriages in linear sliding engagement along the elongated member;
   a plurality of joints, each of the plurality of joints defined along a respective one of the one or more carriages;
   a first cutting device coupled to a first joint of the plurality of joints;
   a second cutting device coupled to a second joint of the plurality of joints; and
   a clamp coupled to the elongated member between the first cutting device and the second cutting device, the clamp configured to grip bone tissue.

2. The apparatus of claim 1, wherein the first cutting device includes an adjustment mechanism for controlling a depth of cuts, the adjustment mechanism including a worm gear for adjusting the depth of cuts.

3. The apparatus of claim 1, wherein the one or more carriages include a tightening knob for restricting linear movement along the elongated member.

4. The apparatus of claim 1, further comprising:
   a first carriage of the one or more carriages positioned along a first end of the elongated member with a first joint of the plurality of joints defined along the first carriage;
   a second carriage of the one or more carriages positioned along a second end of the elongated member with a second joint defined along the second carriage; and
   a third carriage of the one or more carriages positioned along the elongated member between the first carriage and the second carriage, with a third joint of the plurality of joints defined along the third carriage.

5. The apparatus of claim 1, wherein the clamp, the first cutting device, and the second cutting device are each adjustable relative to the elongated member along at least three degrees of freedom.

6. The apparatus of claim 1, wherein each of the plurality of joints further comprises:
   a housing body defined along a respective carriage; and
   a ball stud defined by a ball portion in mechanical communication with a stem portion, wherein the ball portion is rotatably engaged within a cavity of the housing body.

7. The apparatus of claim 6, wherein each of the plurality of joints includes a tightening knob that restricts movement of the ball stud relative to the housing body.

8. The apparatus of claim 1, wherein the first cutting device and the second cutting device each include at least one of a drill, an osteotome, a rongeur, a scalpel, a laser, an ultrasonic device, a chisel, or a saw.

9. The apparatus of claim 1, wherein the clamp comprises a spinous process clamp and defines a first clamp arm and a second clamp arm.

10. The apparatus of claim 1, wherein the first cutting device comprises an osteotome, the osteotome including a blade defining a cutting edge and a mallet end defined along a housing.

11. A method of making an apparatus for incision and extraction of osseous tissue, comprising:
- providing an elongated member defining a stationary portion;
- mounting one or more carriages in linear sliding engagement along the elongated member;
- a plurality of joints, each of the plurality of joints defined along a respective one of the one or more carriages;
- a first cutting device coupled to a first joint of the plurality of joints;
- a second cutting device coupled to a second joint of the plurality of joints; and
- a clamp coupled to the elongated member and configured to grip bone tissue.

* * * * *